United States Patent [19]

Flannery et al.

[11] Patent Number: 4,833,698
[45] Date of Patent: May 23, 1989

[54] APPARATUS FOR THREE DIMENSIONAL TOMOGRAPHY UTILIZING AN ELECTRO-OPTIC X-RAY DETECTOR

[75] Inventors: Brian P. Flannery; Harry W. Deckman, both of Clinton; Peter M. Eisenberger, Morristown; Wayne G. Roberge, Hopewell, all of N.J.

[73] Assignee: Exxon Research and Engineering Company, Florham Park, N.J.

[21] Appl. No.: 891,597

[22] Filed: Aug. 1, 1986

Related U.S. Application Data

[63] Continuation-in-part of Ser. No. 832,145, Feb. 24, 1986, abandoned.

[51] Int. Cl.[4] ...................... G01N 23/00; G01N 23/08
[52] U.S. Cl. .......................................... 378/19; 378/4; 378/901
[58] Field of Search ............................ 378/19, 4, 901; 364/414; 250/369, 370 GX, 370 I, 486.1

[56] References Cited

U.S. PATENT DOCUMENTS 4,298,800 11/1981 Goldman .............................. 378/19
4,521,688 11/1985 Yin ..................................... 250/369

FOREIGN PATENT DOCUMENTS 0166900 8/1985 Japan ................................. 250/486.1
2013068 8/1979 United Kingdom ................. 378/19

OTHER PUBLICATIONS

Flannery, Brian et al., *3-D X-Ray Microtomography*, Science, Sep. 18, 1987, pp. 1439–1444.

*Primary Examiner*—Janice A. Howell
*Assistant Examiner*—Joseph A. Hynds
*Attorney, Agent, or Firm*—Ronald D. Hantman

[57] ABSTRACT

The present invention is an apparatus for producing tomographic images of an object comprising: a beam of collimated radiation transmitted through the object in a plurality of rays, an imaging electro-optic detector for detecting the attenuated transmitted radiation after it has passed through the object, the detector including an energy convertor, image format altering device, and a readout device, wherein the detector has a detective quantum efficiency greater than 0.05, a total signal dependent background less than 10 percent of the signal from the unattenuated x-ray beam, a useful dynamic range greater than 10, a non-uniformity of response between adjacent active pixels of less than 75%, and deviations of geometric linearity that is less than 10 pixels in the recorded image, means for obtaining the attenuation coefficients from the transmitted radiation, and means for computing a reconstructed image of the object from the attenuation coefficients.

16 Claims, 8 Drawing Sheets

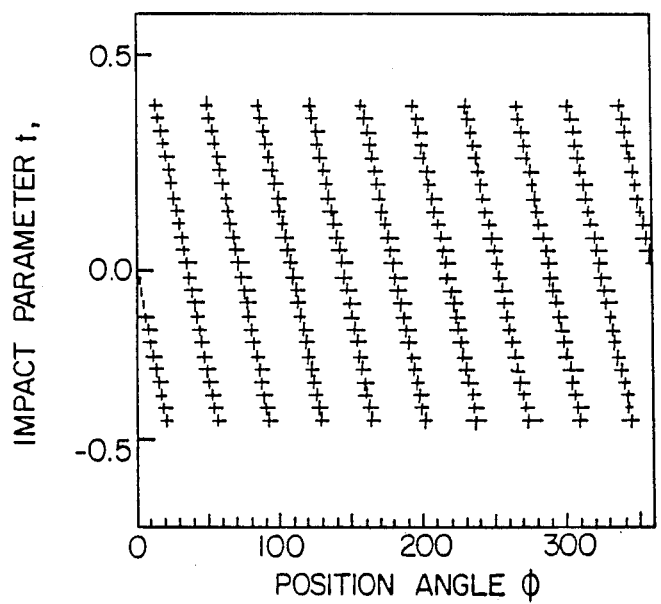
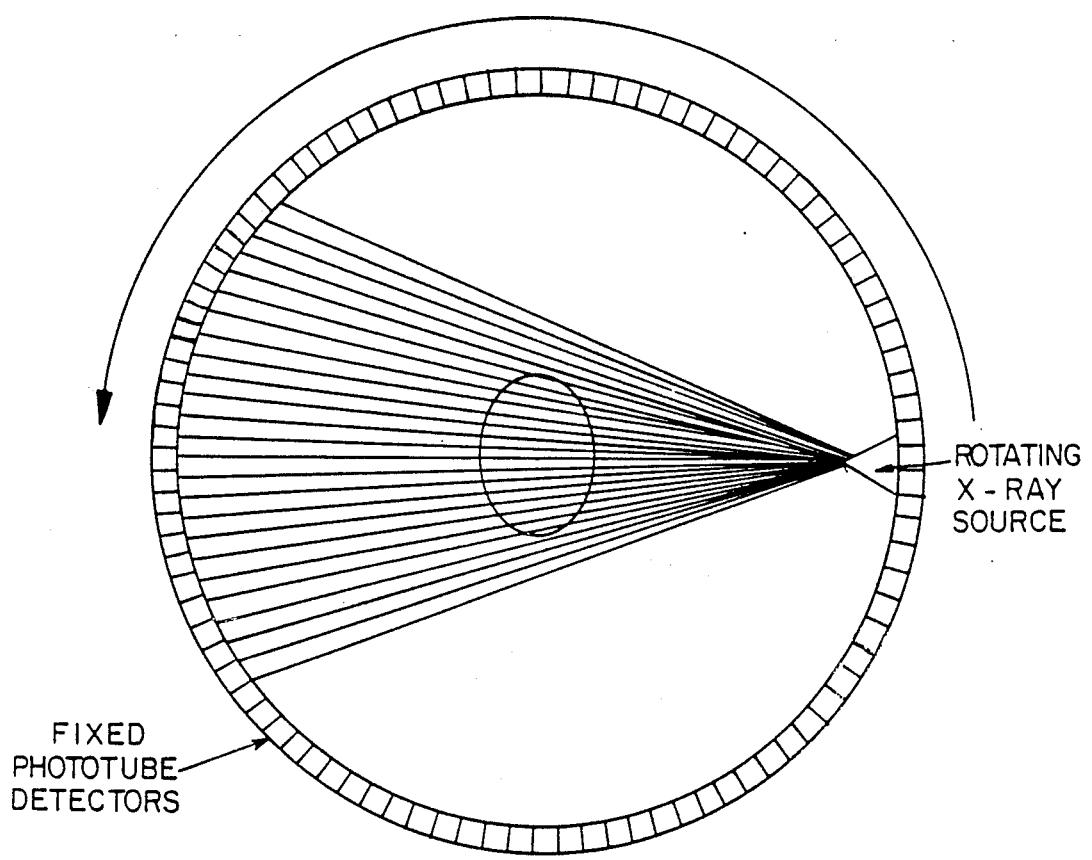
FIG. 2

ELECTRO-OPTIC X-RAY DETECTORS

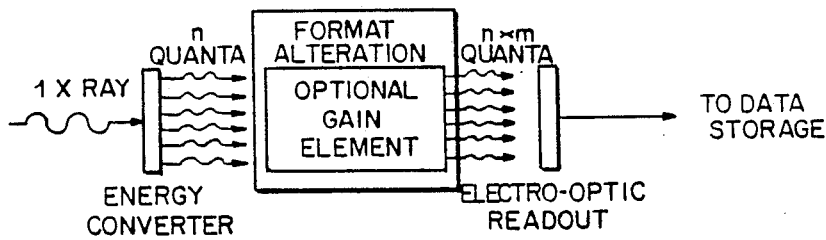

- ENERGY CONVERTERS
    - PHOSPHORS (OPTICAL AND PHOTOELECTRON)

- GAIN ELEMENTS
    - MICROCHANNEL PLATES
    - ELECTROSTATICALLY FOCUSED INTENSIFIER
    - MAGNETICALLY FOCUSED INTENSIFIER

- FORMAT ALTERATION
    - OPTICAL LENS
    - FIBEROPTIC BUNDLES
    - REDUCING IMAGE INTENSIFIER

- ELECTRO OPTIC READOUT
    - IMAGE ORTHOCON      - IMAGE ISOCON
    - VIDICON             - SEC VIDICON
    - SIT                 - SILICON DIODE VIDICON
    - CID                 - RESISTIVE ANODE
    - CCD

FIG. 6

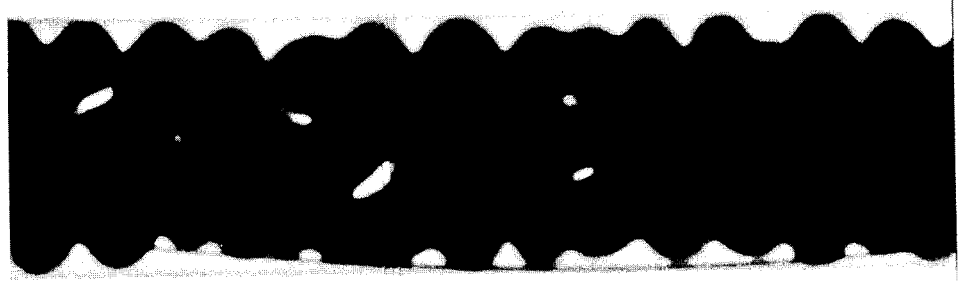
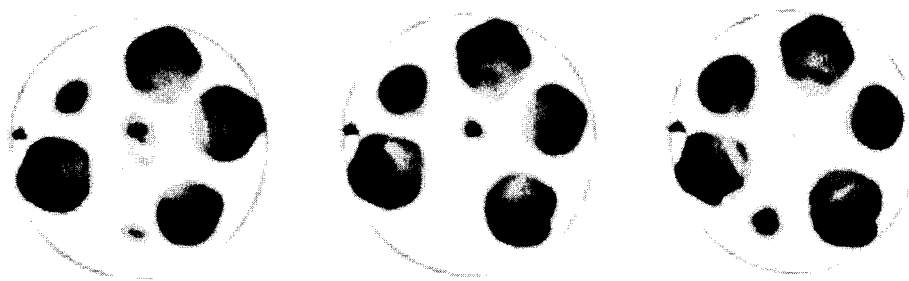
FIG. 8

APPARATUS FOR THREE DIMENSIONAL TOMOGRAPHY UTILIZING AN ELECTRO-OPTIC X-RAY DETECTOR

CROSS REFERENCE TO RELATED APPLICATIONS

This application is a continuation-in-part of U.S. Ser. No. 832,145, filed Feb. 24, 1986 now abandoned.

BACKGROUND OF THE INVENTION

Computerized tomography refers to the procedures used to generate two dimensional maps of some physical quantity in a planar section of a target by measuring and analyzing the attenuation of beams of penetrating radiation passed through the target along sets of coplanar rays. As practiced, a complete apparatus must contain four elements: (1) a source of penetrating radiation, (2) detectors that measure the transmitted intensity of the radiation after passage through the target, and that can be calibrated to give the unattenuated intensity of radiation in the absence of the target, (3) a computational device to store and process the attenuation measurements, converting them into a digital map of attenuation coefficients in the observed plane of the target, and (4) a device to display the resultant image.

Tomography can be practiced in many ways, but the broadest commercial usage is in medical radiology to provide diagnostic maps of bone and tissue structure in human patients (W. Swindell and H. H. Barett, "Computerized Tomography: Taking Sectional X-Rays", Physics Today, pp. 32–41, 1977; C. C. Jaffe, "Medical Imaging", American Scientist, 70, 576 (1982); and P. Alexander, "Array Processors in Medical Imaging", Computer, 16, (1983). Medical CT uses broad band bremsstrahlung radiation from X-ray tubes to produce penetrating radiation that is measured, typically, by scintillation crystals and photo-tubes. Measurements are stored in a programmable digital computer and analyzed using a method generically referred to as convolution (or filtered) back projection (referred to hereafter as FBP). The density map derived from the analysis is displayed on a cathode ray tube as a two dimensional cross sectional image containing approximately $250 \times 250$ elements or pixels, with a resolution of about 1 millimeter, and 1% accuracy in determination of X-ray attenuation coefficient. Medical procedures typically produce scans in only a limited number of adjacent body planes, say one to twenty. Other special purpose tomography probes have been built using different types of ionizing radiation such as gamma rays, and electrons.

An object of the present invention is to provide a microtomography device which uses an intense well collimated beam of radiation to produce three dimensional images with improved spatial resolution. Spatial resolution attainable using the microtomography device can be as small as 0.5 microns which is 100–1000 times better than that achieved with conventional medical CT. A further object of the present invention is to increase the physical scale across the reconstructed image. The microtomography device described is capable of obtaining images with 2 times more resolution elements per plane (physical scale) than conventional medical CT. Increasing the physical scale across the image is especially important in microtomography.

Another object of the present invention is to provide a reconstruction of an object on a three dimensional network of points. Instead of acquiring data in 1–20 adjacent planes (as medical tomographic devices do), the present device acquires data sufficient to reconstruct an image in more than 100 adjacent planes. This provides the ability to obtain three dimensional information about an object. As such the device described herein can be thought of as a three dimensional x-ray microscope.

Improvements in resolution and physical scale of reconstructed images come from design of the detector used to measure the transmitted intensity as well as from the computational technique used to process data. It is an object of the present invention to acquire data using an imaging electro-optic detector. This detector acquires an entire planar image or an entire linear slice of an image having large physical scale with no degradation of counting statistics in each pixel across the image. By acquiring an entire large scale planar image using an electro-optic detector, the data acquisition time and dose delivered to the sample are significantly reduced. Moreover, it is possible to construct electro-optic detectors which have significantly higher spatial resolution than the scintillation detectors used in medical CT. Since the number of data points, N, (resolution elements) acquired in a line across the image can be significantly greater than in medical CT, and data can be simultaneously acquired in multiple stacked planes, it is important to utilize data inversion techniques requiring $N^2$ rather than $N^3$ operations to reconstruct an image. By using data inversion techniques with $N^2$ rather than $N^3$ operations the time required to process the data can be decreased by a factor of more than 100 in many cases.

SUMMARY OF THE INVENTION

The present invention is an apparatus for producing tomographic images of an object. The apparatus includes a plurality of rays of collimated radiation transmitted through the object, an imaging detector for detecting the attenuated transmitted radiation after it has passed through the object, the detector including an energy convertor. Means for obtaining the projection data from the transmitted radiation, and means for computing a reconstructed image of attenuation coefficients of the object from the projection data are also provided. In a preferred embodiment, the imaging detector is an electro-optical detector which also includes an image format altering device, and a readout device, wherein the detector has a detective quantum efficiency greater than 0.05, a total signal dependent background less than 10 percent of the signal from the unattenuated x-ray beam, a useful dynamic range greater than 10, a nonuniformity of response between adjacent active pixels of less than 75%, and deviations of geometric linearity that is less than 10 pixels in the recorded image.

BRIEF DESCRIPTION OF THE DRAWINGS

FIG. 2 is a schematic showing observational paths in a typical medical CT scanner using the "fan beam" observational mode. Discrete observational paths occur at point $(t, \phi)$ as shown in the upper panel.

FIG. 6—Schematic diagram showing the generic components of an electro-optic detector for X-rays. Specific components are enumerated for the energy convertor, optional gain element, format alteration and electro-optic readout.

FIG. 8—Shown at the top of the figure is a single view ($I_p$) of a 750 μm diameter glass capillary tube filled with 200 micron silica spheres and a single room tungsten wire which runs along the tube length. Spatial solution in the image ($I_p$) is approximately ten microns. At the bottom of the figure are cross sectional reconstructions of the tube at the positons indicated by the three lines drawn across the image on top. It is seen that the cross sections of the silica beads are plainly visible in the image. At the left edge of the tube cross section the small dark spot corresponds to the 10 micron tungsten wire.

DESCRIPTION OF THE PREFERRED EMBODIMENT

This invention is broadly an apparatus for computerized tomography. The apparatus includes a detector that can be used in a mode which increases spatial resolution in reconstructed images, below 10 microns. A particular form of the detector can be used to acquire data in multiple stacked planes, allowing the internal structure of a sample to be reconstructed on a three dimensional network of points. In this mode the device described herein functions as a three dimensional x-ray microscope.

Detectors utilized in the present invention form a distinct subset of the broad class of electro-optic detectors for ionizing radiation. Electro-optic X-ray detectors can be broadly defined as position sensitive detectors which utilize components developed for the amplification and recording of optical images. Because of the imaging characteristics of this class of detectors, significantly higher spatial resolutions can be obtained than are possible with scintillation detectors used in conventional tomographic devices.

The invention utilizes a collimated beam of radiation. The radiation must be able to be converted to more easily handled quanta which can be used to form an image within the detector. In general, radiations which fulfill this requirement are ionizing radiations such as X-rays, gamma rays, neutrons and ultraviolet light; however, fluorescent conversion processes for visible light in which no ionized state is formed are included in the definition of radiations which can be used with the present invention. For the purpose of illustration, the present invention will be illustrated using X-rays as the radiation.

Protocols for Data Acquisition

Figure 1:
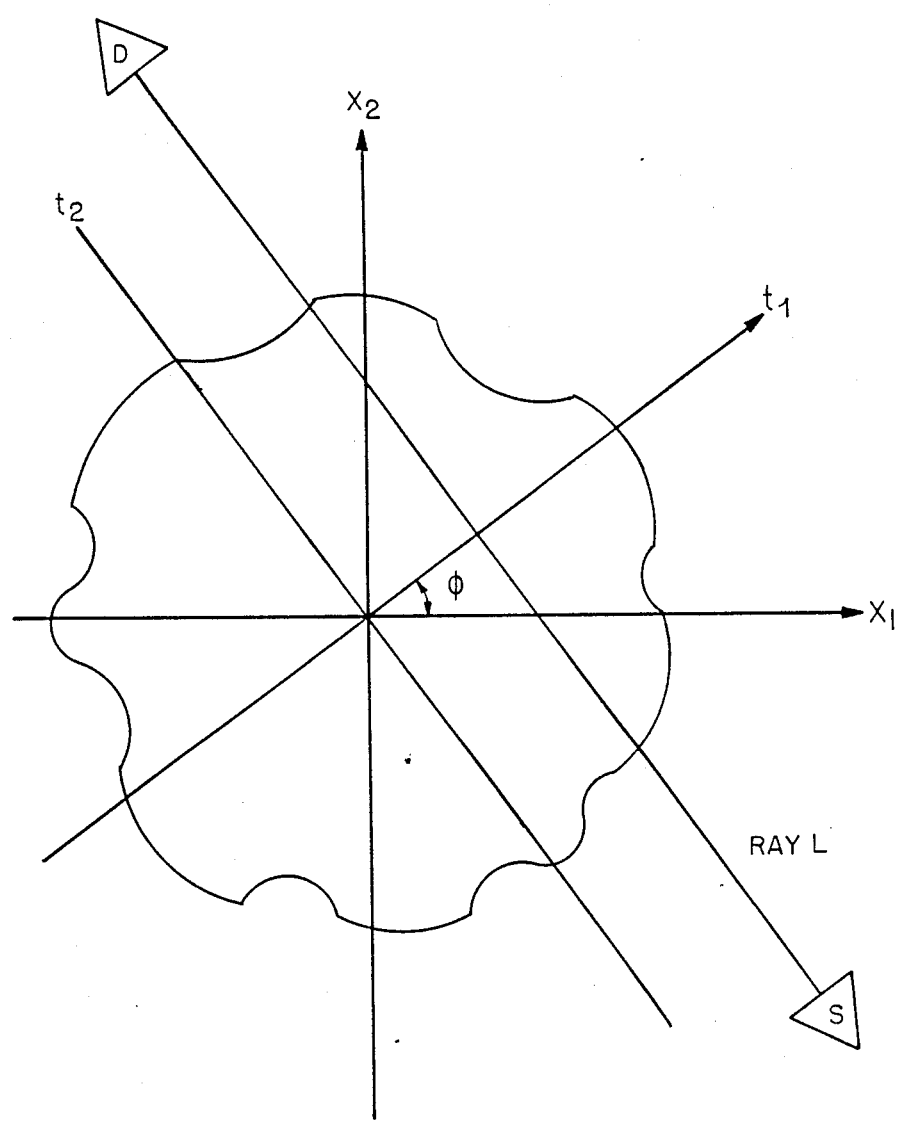
FIG. 1 shows the geometry defining a path through the observed plane of a target. The path L between the source, S, and detector, D, is defined by its impact parameter $t_1$ and angle $\phi$ with respect to a set of fixed cartesian axes $(x_1, x_2)$ in the target.

To generate accurate tomographic images, sufficiently noise-free data must be obtained along a sufficient number of independent coplanar paths through the target (L. A. Shepp and B. F. Logan, "The Fourier Reconstruction of a Head Section", IEEE Trans. Nucl. Sci., Vol. NS-21, pp. 21–43, 1974 and W. Roberge and B. P. Flannery, U.S. Application (Ser. No. 767,902)). Observational paths can be labeled according to their view angle $\phi$ and impact parameter $t_1$, with respect to coordinates fixed in the target, as shown in FIG. 1. In medical tomography measurements are typically obtained with a fixed set of detectors located along a ring surrounding the patient, as shown in FIG. 2. The X-ray source rotates about the ring, illuminating a series of detectors opposite the source with a collimated fan beam of radiation. The opening angle of the collimated X-ray beam is broad enough so that the fan of paths from source to detector completely encompasses the target. For accurate reconstruction of the entire target, the range of impact parameters must span the diameter of the target and the angular rotations must span at least one half of a complete rotation. We refer to the mode of operation shown in FIG. 2 as fan beam collimation.

Figure 3:
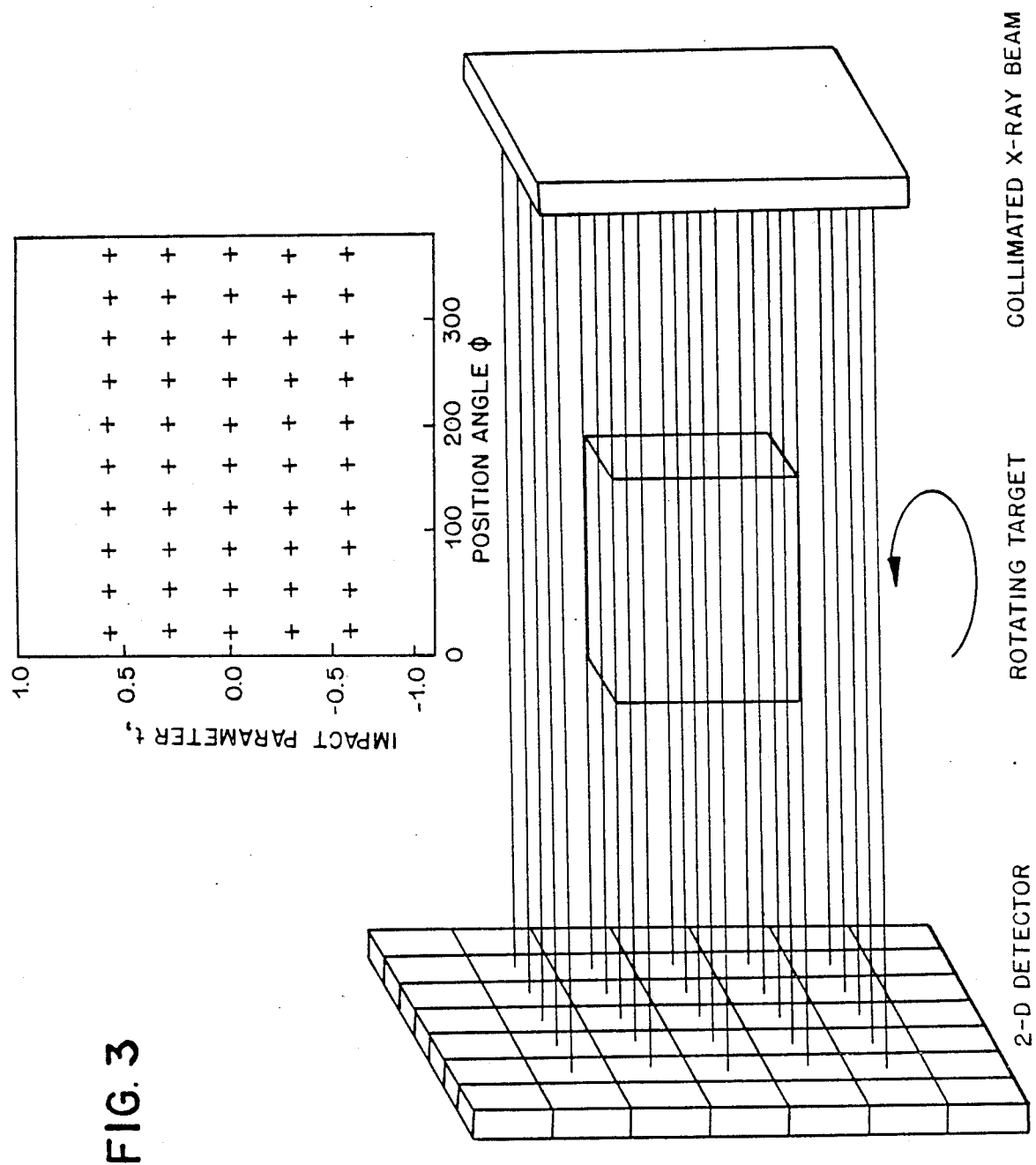
FIG. 3 is a schematic showing observational paths in a scanner using the "parallel beam" observational mode. Here a parallel, collimated beam of radiation irradiates the target in multiple stacked planes and multiple impact parameters simultaneously. The target is rotated for observations at different view angles $\phi$. Discrete observational paths in one of the planes occur at points $(t, \phi)$ as shown in the upper panel.

Another mode of operation for a tomographic scanner is shown in FIG. 3. Collimated X-rays, or other penetrating radiation, illuminate the target along two dimensional sets of plane parallel paths that are recorded by a panoramic electro-optic detector. If a two dimensional imaging electro-optic detector is used, data in multiple stacked planes is measured simultaneously. Views from different angles are achieved by rotating the target (as shown in FIG. 3) or by rotating both source and detector around a stationary sample. Data taken in this geometry are said to be taken with plane parallel collimation. The plane parallel mode of data acquisition is clearly preferred when high spatial resolution between 0.5 and 25 microns is selected. For high spatial resolution data acquisition, X-ray beams can be readily collimated for the plane parallel mode shown in FIG. 3, whereas appropriate collimation for the fam beam geometry is difficult. Throughout this application, we will illustrate the use of electro-optic detectors with the plane parallel mode of data acquisition. However, the invention is also applicable to the fan beam mode of data acquisition.

Projection Measurements and Inversion Methods

Observation time required and quality of images produced with the device depend sensitively on composition and size of the target, characteristics of the source, and performance of the detector. In general observational conditions must be obtained to either optimize the source spectrum for a given sample, or adjust the sample size to optimize for a given source spectrum. Optimum observational conditions are determined by signal to noise considerations for tomographic images.

These signal to noise considerations also place limits on several aspects of detector performance, limiting the types of electro-optic detectors which are suitable for use in tomographic scanners to a small subset of the broad electro-optic detector class. To determine restrictions on the types of electro-optic detectors which can be utilized, we analyze sources of noise in tomographic images.

Noise in tomographic images arises from two sources: (1) noise in the data, and (2) noise amplification introduced by the inversion method. The basic data consist of measurements of the attenuation of a signal, typically an X-ray beam, passed through the target along many coplanar rays, (L. A. Shepp and B. F. Logan, "The Fourier Reconstruction of a Head Section", IEEE Trans. Nucl. Sci., Vol. NS-21, pp. 21–43, 1974). FIG. 1 defines Cartesian coordinates in the frame of the target and a scanning device oriented to view the target from an angle $\phi$. Here $(\phi, t_1)$ define positions perpendicular to and along the path of the beam. For accurate inversion the attenuation measurements must have adequate signal-to-noise, and geometrical coverage of the scanbeams must fill the $(\phi, t_1)$ plane densely enough to give the desired resolution.

In the mode of operation preferred for high spatial resolution, data is obtained as M discrete, equally spaced view angles spanning $0 \leq \phi < \pi$, and N equally spaced, discrete, parallel impact parameters spanning $-D/2 < t_1 < D/2$, where D is the projected diameter of the target. The image recovered is divided into the pixels corresponding to a size, $\Delta t$, which in a preferred embodiment have $\Delta t = D/N$. Resolution in the reconstruction cannot exceed the pixel size $\Delta t$, and the rotation between views $\Delta \phi$ should be such that $D\Delta\phi/2 \leq \Delta t$, i.e. $M \geq \pi N/2$. Data in this format can be used to reconstruct an image of the observed plane covering an area $D^2$ on a grid of order $N \times N$ pixels each corresponding to a size $t^2$. Thus, $\sim 2N^2$ observations are used to map the target at $\sim N^2$ points. For targets with unknown structure this degree of coverage in $(\phi,t)$ must be available to reconstruct the image with resolution corresponding to $\Delta t$. It should be noted that the $N^2$ pixels of a section are usually displayed on a cathode ray tube and are not separated physically by a distance $\Delta t$, but separated by a magnification factor, m times $\Delta t$. However, targets wih known symmetry require fewer views, e.g., projections from a single view suffice to reconstruct images of rotationally symmetric targets.

In transmission tomography the intensity of the incident $(I_O)$ and detected $(I_D)$ beam are related by attenuation along the path through the target. In the absence of scattering $$I_D = I_0 \exp[-\int F(t_1,t_2)dt_2]$$  Eq. 1 where $F(t_1,t_2)$ is the linear attenuation coefficient in the target, and the integration over $t_2$ traverses the beam's path (see FIG. 1). The quantity actually used in tomographic analysis is the optical depth or "projection" $P(\phi,t_1)$ defined as $$P(\phi,t_1) = \ln [I_O(\phi,t_1)/I_D(\phi,t_1)].$$  Eq. 2

The apparatus measures both $I_O$ and $I_D$. This is achieved through use of a suitable calibration procedure.

The goal of tomography is to recover $F(x,y)$ from measures of its line integral $P(\phi,t_1) = \int F dt_2$. In general, inversion methods reconstruct the attenuation coefficient $F(x,y)$ at a point as a linear weighted summation of the measured projection data $$F(x,y) = \Sigma_m \Sigma_n w(x,y;\phi_m,t_n) P(\phi_m,t_n)$$  Eq. 3 where the weights $w(x,y;\phi,t)$ depend on the position in the target and the orientation of the scan. Eq. 3 indicates that the scan data can be inverted to evaluate $F(x,y)$ at any arbitrary point inside the target.

Initial reconstruction methods for medical tomography used an interative procedure (see U.S. Pat. No. 3,778,614) to recover the attenuation coefficients $F(x,y)$. Starting with an arbitrary initial trial solution, the method computationaly derived values for projection data that would occur from the trial image. Differences between the measured and derived projection data were used to correct the trial image successively until sufficient agreement was obtained between computed and observed projections.

Later, the far better method of Convolution Backprojection [also referred to as Filtered Backprojection (FBP)], was developed and applied in a tomography apparatus (L. A. Shepp and B. F. Logan, "The Fourier Reconstruction of a Head Section", IEEE Trans. Nucl. Sci., Vol. NS-21, pp. 21–43, 1974 and C. A. G. LeMay, U.S. Pat. No. 3,924,129. Filtered backprojection (FBP) has become the universally practiced method for commercial tomographic reconstruction. It is directy applicable to both the fan beam and plane parallel modes of data acquisition.

Another method for reconstructing utilizes Direct Fourier Inversion Methods (DFI). Its essential advantage over FBP is that the number of mathematical operations required to invert data to form an image of size $N \times N$ pixels scales as $N \times N \times N$ in FBP but only $N \times N \times \log_2 (N)$ in the DFI method. For example the DFI method inverts data 40 times faster than FBP for images containing $256 \times 256$ pixels and its relative speed advantage grows for larger images.

Figure 4:
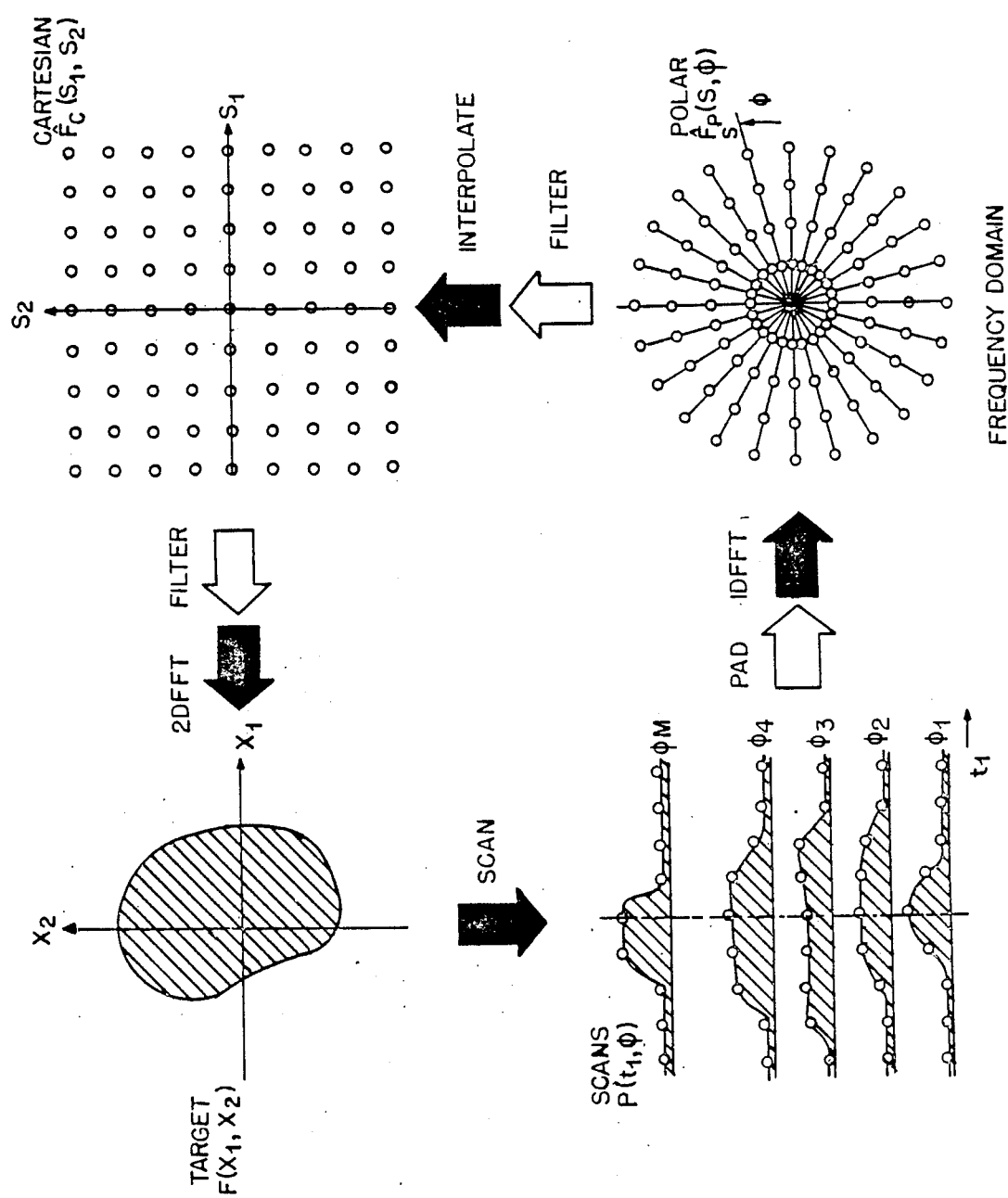
FIG. 4 is a schematic of the steps of the Direct Fourier Inversion Method showing the relation between the target and its projections in signal spaces and the representations of the Fourier transform of the target in polar and Cartesian coordinates.

Basis of the DFI method stems from mathematical analysis that shows the two dimensional Fourier Transform of the target and the one dimensional Fourier Transforms of the projected images of the target are identical. This result, known as the Projection-Slice theorem, applies to exact continuous representations of the target and its projections. In practical applications tomography works with noisy discrete measurements of projections. Recently techniques have been developed by W. Roberge and B. Flannery (U.S. application Ser. No. 767,092) to implement inversion of discrete data with Fourier Transforms. FIG. 4 shows the key steps involved in the implementation of Direct Fourier Inversion (DFI). From the projection data it is straightforward to determine the Fourier coefficients of the target along a series of discrete points arranged on a polar raster: coefficients are given at equally spaced points along sets of rays from the coordinate origin in frequency space (see FIG. 4). However, to carry out a reconstruction efficiently, it is necessary to know the Fourier coefficients along sets of points distributed in frequency space in a Cartesian raster. Thus, efficient Fourier methods in tomography require a procedure for interpolation from a polar raster to a Cartesian raster. Inaccurate interpolation produces artifacts in the image, and can result in noise amplification. One of the key aspects of DFI implementation is the development of rapid highly accurate interpolation methods. Another important detail of the method is that the Fourier coefficients depend on the coordinate origin chosen for the spatial measurements. It is necessary to shift all transforms so that the origin corresponds to a common point. That origin is given by the point at which the rotation axis defining the view angles intercepts the target plane. Without the origin shift, the phases of the Fourier coefficients become scrambled in the inversion. Thus, the basic steps of the Direct Fourier Inversion Method are:

(1) 1D FFT: For projection data at a given angle, obtain the discrete, one dimensional Fast Fourier Transform with respect to the impact parameter. The result gives Fourier coefficients along a ray in signal space at equally spaced intervals from the origin up to some maximum frequency.

(2) Phase Shift to Target Origin: Bring the phase of the coefficients obtained in step (1) into agreement with a positioning convention that places the spatial coordinate origin at the axis about which the view angle was rotated.

(3) Fill Polar Raster: Repeat steps (1) and (2) for the projection data at each new view angle to build up the Fourier coefficients along a series of rays as shown in FIG. 4.

(4) Interpolate to Cartesian Grid: By interpolation determine values for the Fourier coefficients at equally spaced points in the two dimensional Cartesian grid.

(5) Phase Shift to Cartesian Origin: Perform a phase shift from the origin at the target center to an origin at the lower left corner of the square region in which the image will be constructed, as required by the convention for locating the origin in two dimensional FFTs.

(6) Inverse Fast Fourier Transform: Use the inverse FFT to convert from the frequency domain of the Fourier Transform back to signal space producing an image of the target.

In the basic form described above in steps 1-6 the DFI method can produce acceptable images only for targets in which the attenuation coefficient varies smoothly. However, numerous studies have found that the method produces unacceptable images for practical targets, such as are found in medical applications, where sharp density variations are encountered between bone and soft tissue. Problems arise from inaccuracy in the interpolation procedure, and from the basic problem that Fourier analyses tend to produce oscillatory artifacts when they encounter sharp discontinuities. Taken together these problems introduce unacceptable distortion and artifacts into the reconstructed image.

Related problems also affect reconstructions obtained using back projection methods. In fact, low-pass filters must be applied to correct artifacts that would otherwise contaminate the image generated by back projection methods without filtering.

Roberge and Flannery discoverd (U.S. application Ser. No. 767,902) a means to improve the DFI method to such a degree that it produces acceptable images that are comparable in quality with results obtained by FBP, while still maintaining the enormous speed advantage of DFI. Those steps are labeled by the terms "padding" and "filtering" in FIG. 4.

PADDING: prior to step (1) above we "pad" the projection data by adding additional data at impact parameters both smaller and larger than were actually observed. Since the target does not extend beyond the observed range of impact parameters, the values for the padded data do not need to be estimated; they are known exactly to be zero. Thus, by padding we are not introducing an approximation, we are using additional known information. We also use padding to assure that the number of data points in the projection are an integral power of 2, as required for optimum use of the FFT.

By padding we obtain values for Fourier coefficients at more points along the ray in the polar raster. Because we have no additional resolution the maximum distance of points from the origin in frequency space is not increased, but the number of points between the origin and the last frequency point increases by the padding factor. For instance, if we observed projection data at 256 impact parameters and padded the data by adding zeros at 256 more points, than we obtain 257 values for Fourier coefficients between the origin and the most distant point, rather than 129 without padding. Furthermore, the values at the intermediate points are approximately those values that would have been obtained using high order interpolation based on analyses of the behavior of Fourier coefficients at frequencies intermediate between discrete values. To apply those interpolation formulae at arbitrary intermediate points is possible, but computationally expensive. By padding we achieve the same accurate interpolation along rays and get points at many intermediate frequencies using the FFT algorithm itself. It is possible to adjust the amount of padding to meet the needs of the particular target being analyzed. By this step the interpolation procedure becomes far more accurate.

FILTERING: In order to remove or minimize the artifacts corresponding to oscillations introduced by using Fourier methods, a number of standard low pass digital filters have been developed. We find that the use of a standard low pass filter, e.g., the Hanning filter with adjustable cutoff frequency, effectively removes high frequency oscillations in the image. The Hanning filter smoothly reduces the amplitude of the Fourier coefficients by a factor $Y(s)$ that varies smoothly from 1 to 0 as frequency grows from 0 to $s_c$:

$$Y(s) = \begin{cases} \frac{1}{2}(1 + \cos(\pi s/s_c)) & \text{if } s < s_c \\ 0 & \text{if } s > s_c \end{cases}$$

By choice of $s_c$ one can selectively adjust the cutoff of high frequency variations. (Note that the choice of low-pass filter in FBP methods serves the identical purpose). Filtering can be applied to the Fourier coefficients in either the polar or Cartesian grid, or both. Filtering essentially corresponds to averaging the reconstruction over length scales inversely proportional to the cutoff frequency. Viewed in this way it can readily be shown that filtering sacrifices resolution in order to improve the relative accuracy of values for the X-ray attenuation coefficient in the reconstruction. The choice of cutoff frequency $s_c$ can be chosen to adjust the degree of smoothing selectively.

It should be noted that the choices of filters can result in additional computational savings. It is unnecessary to evaluate Fourier coefficients beyond the cutoff frequency, or to carry out the inverse Fourier Transform for an unnecessarily large set of coefficients. For example, suppose that data was obtained sufficient to reconstruct the image on a grid of 512×512 pixels, corresponding to a maximum frequency s(512), but the filter step needs to eliminate ½ the frequencies. Then the Fourier coefficients in the Cartesian grid need only fill an array of 256×256 points and the inverse transform can be carried out more rapidly using the smaller set 256×256 Fourier coefficients.

For data taken using the protocols described above, it only makes sense to evaluate the reconstruction on a grid with point spacing $(\Delta x = \Delta y) \geq \Delta t$. Furthermore, practical inversion methods always introduce additional smoothing by a convolution or filtering step that reduces the effective resolution still more. The tradeoff involved is that low pass filters enhance signal-to-noise at the expense of degrading resolution.

Signal to Noise Considerations

For a discussion of signal-to-noise it is useful to define $\Delta x$ to be a spacing characteristic of the meaningful resolution allowed by the reconstruction. For FBP methods $\Delta x$ is given by the bandwidth used in the convolution step (D. A. Chesler, S. J. Reiderer, and N. J. Pelc, "Noise due to Photon Counting Statistics in Computed X-Ray Tomography", J. Comput. Asst. Tomagr., VI, 64–74, 1977. For DFI methods $\Delta x$ is approximately the inverse of the cutoff frequency used in filtering.

While the propagation of noise from data to reconstruction can depend on peculiar features of the target itself that might introduce correlations into the reconstruction, general trends can be analysed objectively in terms of the algorithmic operations involved in the reconstruction. We define $\omega$ to be the ratio between noise-to-signal in the data and reconstruction, $$[\sigma_F/F]/[\sigma_P/P] \equiv \omega(D, \Delta x, \Delta t) \quad \text{(Eq. 4)}$$

where we assume that the projection data are all typical magnitude P containing noise that can be described as normally distributed with standard deviation $\sigma_P$, and where F, $\sigma_F$ are the typical value of the linear attenuation coefficient and its standard deviation.

Analyses to determine $\omega$ have been carried out by D. A. Chesler, S. J. Riederer, and N. J. Pelc, ["Noise due to photon counting statistics in computed X-ray tomography", J. Comput. Asst. Tomogr., 1, 64 (1977)], for the FBP method and by W. Roberge and B. Flannery [U.S. application Ser. No. 767,092] for the DFI method. For both algorithims the amplification factor can be expressed as $$\omega^2 = B \left[ \frac{D \Delta t}{\Delta x^2} \right] \quad \text{(Eq. 5)}$$

where B is a numerical coefficient of order unity that depends on details of the algorithim. Since inversion usually is applied near the resolution limit $\Delta x = \Delta t$ allowed by the scan data, Eq. 5, shows that noise amplification scales approximately as the square root of the number of pixels per side in the reconstruction, $K = D/\Delta x$, so that $\omega$ scales as $\sqrt{K}$ or $\Delta x^{-\frac{1}{2}}$. To image a target with higher resolution while maintaining fixed signal-to-noise requires more observations and higher accuracy. For example, to double the resolution at a fixed accuracy not only must measurements be made along four times as many paths, but also the signal-to-noise of each observation must be higher by $\sqrt{2}$. Eq. 5 also shows that methods that "average" the reconstruction, $\Delta x > \Delta t$, reduce noise. For instance, reconstructions that average 4 points, $\Delta x = 2\Delta t$, have $\frac{1}{2}$ the noise.

At the start of this section we noted that noise in tomographic images arises from two sources. The previous discussion quantified noise amplification introduced by the inversion method. Now we consider observational uncertainty in the data. Observational uncertainties in the data come from X-ray counting statistics as well as noise introduced by the detector. The two related measures of the accuracy, $\rho$, and the detective quantum efficiency, D, may be used to quantify the amount of noise a detector adds to the X-ray signal. They are defined as $$\rho = \frac{\sigma_o}{S_o} \quad \text{(Eq. 6)}$$

and $$G = \left(\frac{S_o}{\sigma_o}\right)^2 / \left(\frac{S_i}{\sigma_i}\right)^2 \quad \text{(Eq. 7)}$$

where S means integrated signal, $\sigma$ = RMS integrated noise, and subscripts o and i refer to output signal of the detector and input X-ray signal, respectively.

In what follows we shall assume S and $\sigma$ are in units of number of X-ray photons and that the photon source obeys Poisson emission statistics, i.e., photons are emitted at a constant average rate but at random times. Then the two measures are uniquely related by $$\rho = \frac{1}{\sqrt{\frac{S_i G}{\sigma_i}}} \quad \text{(Eq. 8)}$$

We call $S_i$, the input number of X-rays needed to make the measurement, the dose. In general, both $\rho$ and G are functions of the dose, $S_i$, and a set of variables $(r_j, j=1, \ldots, n)$, which depend on the detector. Typical $r_j$ might be the area over which the signal is integrated, the integration time, the dose rate, etc. Given a plot of $\rho(S_i, r_j)$ one may derive a plot of $G(S_i, R_j)$ and vice versa. Consequently, a choice between the two measures is based largely on convenience.

The detective quantum efficiency has been used for years by the electro-optics industry as a characterization of imaging devices. Its use as a measure of two dimensional X-ray detector efficiency has been discussed by S. M. Gruner and J. R. Milch [Transaction Amer. Crystallographic Assoc., V. 18, p. 149 (1982)]. It describes the added noise introduced by the detector relative to an ideal detector. The output statistics of the ideal detector are defined equal to the input signal statistics, i.e., $$\frac{S_o}{\sigma_o} = \frac{S_i}{\sigma_i} \quad \text{(Eq. 9)}$$

in which case G = 1. The degree to which G is less than 1 indicates the fractional manner in which the detector is less than ideal. For the electro-optic X-ray detector used in the microtomography system it is preferred that G be greater than 0.05. It is more preferred that G be greater than 0.5.

If the detector is exposed for a time T, then the total number of photons incident to the detector is $N_D I_D T$, and the standard deviation $\sigma_N$ expected for N photons is $\sigma_N = N^{\frac{1}{2}}$. If on average the number of counts observed in a time T ought to be $\bar{n}$, then the measured number will be $n = \bar{n} + \tau[G\bar{n}]^{\frac{1}{2}}$ where $\tau$ is a normally distributed random variable. Then the measured projection will contain Gaussian noise according to $$P = \bar{P} + \tau[\bar{N}_D G]^{-\frac{1}{2}} \quad \text{(Eq. 10)}$$

where $\bar{P}$ is the average expected value.

For a target of typical diameter D and average linear attenuation coefficient $\bar{F}$, the results assembled so far determine $N_O$, the number of incident photons per detector needed to produce an image of given pixel size with signal-to-noise ratio $F/\sigma_F$. Equations 1 and 2 show that $P = \bar{F}D$, and that $N_D = N_0 \exp(-\bar{F}D)$. Then from Eq. 4 we find that $$\left[\frac{N_0}{\omega^2}\right] = \frac{\exp(\bar{F}D)}{G^2[\bar{F}D(\sigma_F/F)]^2} \quad \text{(Eq. 11)}$$

Recall that the amplification factor $\omega$ (see Eq. 5) depends essentially on the image size in pixels. Thus, for an image of given pixel size and accuracy, $\sigma_F/\bar{F}$, $N_0$ depends only on the optical depth $\bar{F}D$ through the target.

Figure 5:
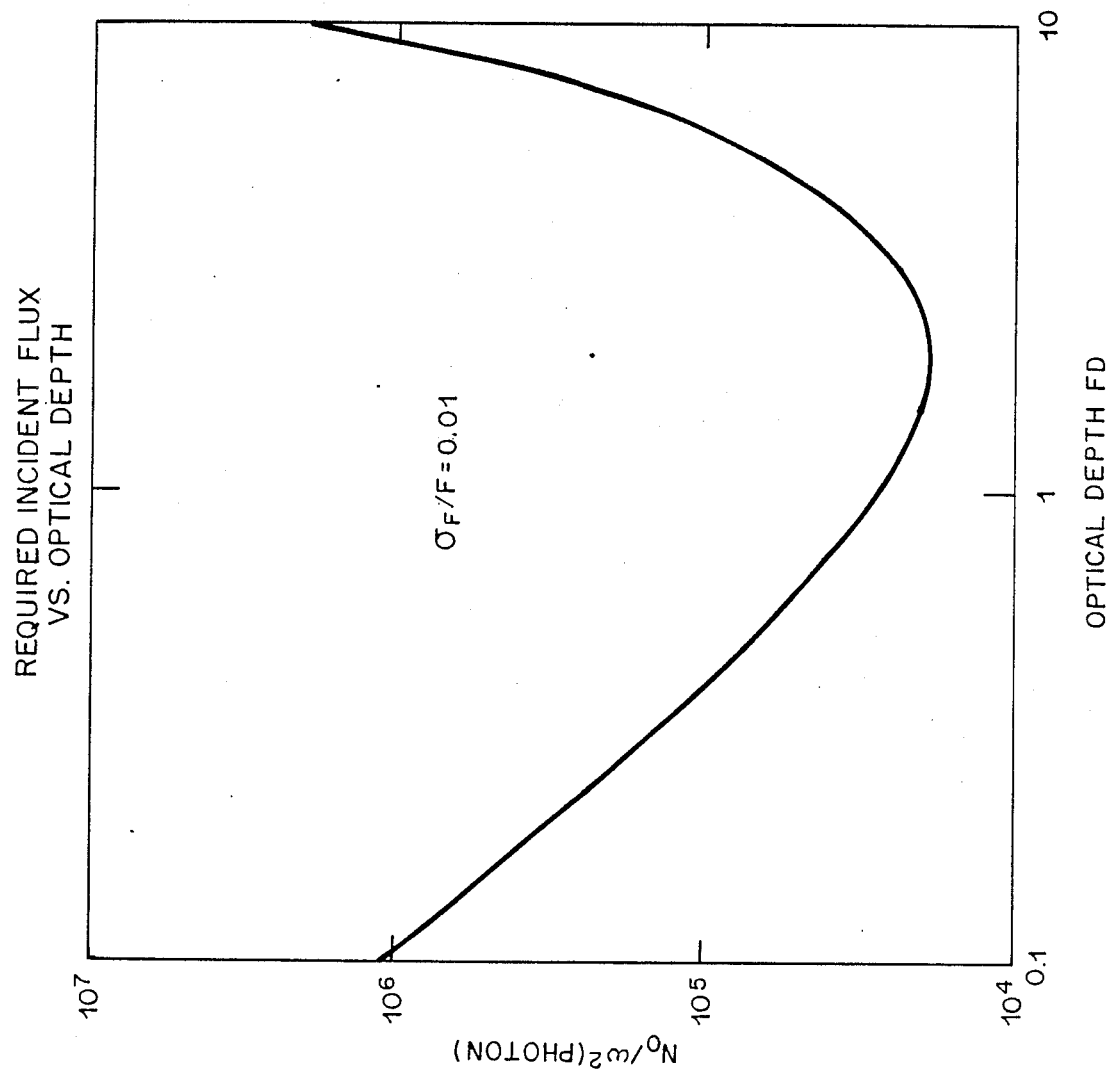
FIG. 5—Incident photons, $N_O$, required per projection measurement plotted as a function of optical depth through the target, FD. For Possion counting statistics, $N_O$ incident photons are needed to provide sufficient accuracy for reconstruction of a tomographic image with relative accuracy $\sigma_F/F=0.01$. The factor is the ratio between relative accuracy in the image and projection data. For a Direct Fourier Inversion of an image with $100 \times 100$ pixels, $\omega^2$ is greater than 10.

As shown in FIG. 5, $N_0$ is a minimum for optical depth $\bar{F}D = 2$. The plot shown in FIG. 5 is for a signal to noise ratio $\sigma_F/F = 0.01$, however similar behavior is found for all useful signal to noise ratios. This occurs because the actual signal depends on the number of photons absorbed by the target. For large optical depth, $\bar{F}D >> 2$, $N_O$ grows because a few photons are transmitted. For small optical depth, $\bar{F}D << 2$, $N_O$ grows because few photons are absorbed.

Further substitution for $\omega$ from Eq. 5 into Eq. 11 gives an expression for $N_0$ when the image is reconstructed on a grid of $D/\Delta x$ pixels per side:

$$N_0 = B\left[\frac{D}{\Delta x}\right]\left[\frac{t}{\Delta x}\right]\frac{\exp(\bar{F}D)}{G^2[\bar{F}D(\sigma_F/F)]^2} \quad \text{(Eq. 12)}$$

For example, to image a target of optical depth $\bar{F}D = 1$, with relative accuracy $\sigma_F/F = 0.01$, on a grid of size $100 \times 100$ pixels requires $N_0 \cong 10^6$ incident photons per pixel in the detector (when $\Delta x = \Delta t$).

X-Ray Source Requirements

The previous discussion shows that $N_0$, the number of photons incident per pixel required to produce an acceptable tomographic image depends sensitively on the optical depth ($\bar{F}D$) which varies strongly with sample size, composition, and beam energy. Optimal observation conditions occur when $\bar{F}D = 2$. The preferred range of optical depths lies between $\bar{F}D = 0.2$ and $\bar{F}D = 6$. A more preferred range of optical depths for sample observation lies between $\bar{F}D = 0.8$ and $\bar{F}D = 3$. This range of observational conditions can be attained either by altering the X-ray beam energy or the sample size. The sample size is $D = N\Delta t$ where N is the number of pixels across the object and $\Delta t$ is the spatial resolution of each pixel. For the tomography systems described herein, N is in the range of 20 to 5,000 pixels. A more useful range of N lies between 100 and 1000 pixels. The maximum attainable resolution for the tomography system described herein is 0.5 μm and the minimum attainable resolution is approximately 5 mm. A more preferred mode of operation of the instrument provides resolution ($\Delta t$) in the range of 1-100 microns. The minimum sample size which can be accommodated by the instrument is 10 pixels $\times$ 0.5 microns = 5 microns and a more preferable minimum sample size is 100 pixels $\times$ 1 micron = 100 microns. To operate the instrument near optimal observation conditions ($\bar{F}D = 2$) with samples having dimensions greater than or equal to the minimum sample size, the linear X-ray absorption coefficient, ($\bar{F}$), through the sample, should be less than 1,000 cm$^{-1}$ or more preferably less than 200 cm$^{-1}$. To obtain linear X-ray absorption coefficients ($\bar{F}$), below these limits, the X-ray energy should in general be greater than 1 kev and more preferably greater than 5 kev. These limits are derived from the mass attenuation coefficients of X-rays in matter which can be found several standard references including the *Handbook of X-rays*, edited by E. F. Kaelble (published by McGraw Hill Book Co., N.Y., 1967).

Sources of X-rays with energies greater than 1 to 5 kev include synchrotrons, rotating anodes, X-ray generators and X-ray tubes. To use these sources of radiation in the preferred embodiment of the microtomography system described herein, the X-ray beam generated must be conditioned so that it is plane parallel with a predetermined spectral distribution. Parallelism of the rays is required due to the nature of the reconstruction algorithms which require that rays pass through only a single column of pixels in the sample. As such, a principal ray passing through the sample (see FIG. 3) must be parallel with any other ray through another point in the sample an accuracy given by $$\alpha < \frac{\Delta t}{D} \times 2 \quad \text{(Eq. 13)}$$

where $\alpha$ is the maximum angular deviation of two principal rays through different points in the sample, $\Delta t$ is the minimum resolution element in the image and D is the distance the X-ray beam travels through the sample. Divergence of any two rays passing through the same point in the sample is limited by penumbral blurring of the shadow cast onto the detector. To maintain desired resolution, the divergence of the two rays through the same point in the sample must be such that $$\alpha' \leq \frac{\Delta t}{S} \quad \text{(Eq. 14)}$$

where $\alpha'$ is the angular divergence of two rays through the same point in the sample and S is the distance from the sample to the first energy conversion element in the detector.

Different collimation techniques can be used to achieve this degree of parallelism and beam divergence for rotating anodes and X-ray tubes. Collimation can be achieved by using either a monochromater, physical collimator or distance to limit the angular beam spread through the sample. Collimation increases as the distance between sample and source is increased. If the effective source size at the X-ray generator is $S_{generator}$, the distance a sample must be placed away from the generator, $D_{generator}$, (determined from Equation 14) is $$D_{generator} > \frac{(S_{generator})}{\Delta t} S \quad \text{(Eq. 15)}$$

Collimation can also be achieved by placing in the beam, either a grazing incidence X-ray mirror, layered synthetic multilayer monochromater, flat crystal monochromater or curved crystal monochromater. Positioning of these X-ray optical elements should be such that both Eqs. 14 and 15 are satisfied and flux through the sample maximized to the greatest extent possible. Choice of collimation method used for rotating anodes and X-ray tubes is dictated not only by these requirements but also by the degree of spectral purity required for accurate image reconstruction. Spectral purity in beams collimated with distance can be achieved by filtering of the radiation. For instance, a nickel filter can be used with a Cu X-ray tube to improve the spectral purity. For synchrotron radiation, the angular distribution of radiation eminating from the ring is sufficiently small that in many cases no additional collimation is required. However, because of the high brightness of synchrotron sources, it is usually desirable to utilize a monochrometer to improve the spectral purity of the radiation.

Electro-Optic X-Ray Detector Performance Criteria

Several methods exist for direct recording of 2-dimensional X-ray images with 1–10 μm spatial resolution. Two dimensional X-ray images can be directly recorded in film with 1–10 μm resolution. Unfortunately, the silver halide grain structure in film introduces a noise such that the maximum attainable signal to noise ratio is unacceptable for tomography. Two dimensional X-ray images can also be obtained by directly bombarding solid state detectors such as charge coupled devices and programmable read only memories. Unfortunately, commercially available solid state devices tend to degrade after approximately $10^9$ X-rays per pixel have been acquired. To circumvent those problems and record high resolution two dimensional images, we utilize an electro-optic X-ray detector which employs components developed for the amplification and recording of optical images.

The generic detector, as depicted in FIG. 6, consists of four elements: an energy converter, an optical gain element, a device to magnify or demagnify the image (i.e., an image format altering device) and a readout device. The function of the energy converter is to distribute the energy of the X-ray photon amongst numerous, more easily handled quanta. Typically, it is a phosphor screen which produces visible light. In some cases, it may be an electron emitting X-ray photocathode. Often, the quanta produced in the converter are still too few in number to be effectively recorded in the readout device; consequently, a gain element may be interposed. Typical gain element are magnetic or electrostatically focused image intensifiers or microchannel plates. The format of the output from the gain element (or phosphor must usually be altered before it is recorded) with an imaging readout device. Format alteration is necessary because the image from the gain element or phosphor usually differs in size from the readout device. Hence it is usually necessary to couple the two via magnifying or reducing mechanisms. Magnification or demagnification of the image can be accomplished with either electron or light optics. Light optic format alterations can be accomplished using either lens or fiber optic coupling. With electron optics, format alterations can be obtained from electrostatic focusing in an image intensifier. The readout devices are the most diverse class of elements in electro-optic detectors. They range from a bewildering assortment of vacuum tubes, to solid state detector arrays, to resistive anode devices, several of which are listed in FIG. 6. Only a few of the tremendous number of configurations for the different converter, gain, and readout elements available are suitable for use as a quantitative detector needed in tomography, even though most configurations can produce a visually pleasing image. Limitations on the number of electro-optic detector configurations which can be used in tomography stem from the following detector attributes:

(1) Quantam detection efficiency, (2) signal dependent backgrounds in the recorded image, (3) useful dynamic range of the detector, (4) spatial uniformity of response (quantum uniformity), (5) positional linearity (geometric linearity). These performance criteria must have a particular range of values to make a two dimensional x-ray detector suitable for a tomographic system. Applicable ranges of these performance criteria are discussed in subsequent paragraphs. In the subsequent discussion performance criteria will apply to active pixels (or non-defective pixels). In any device there will be a small number of defective pixels, which may be characterized as having a quantum efficiency degraded by more than a factor of about 10 from the average. These are referred to as "bad pixels" and are specifically excluded from the subsequent discussion. Limitation on the number of bad pixels which can be present in the detector is such that no more than 20% of the pixel rows running perpendicular to the system axis of rotation contain a bad pixel within the sample image. In a more preferred embodiment no more than 1% of the pixel rows running perpendicular to the system axis of rotation contain a bad pixel within the sample image.

Quantam detection efficiency needed in the electro-optic detector is determined by signal to noise considerations in the reconstructed signal.

It was previously shown that the number of photons, $N_0$, required to reconstruct an image with a given signal to noise ratio scales as $1/G^2$ (Equation 12). Thus, reductions in G, significantly lengthen the time required for a tomographic scan. If G is as small as 0.05, the time required for a tomographic scan will be increased by a factor 400 compared with an ideal detector. Because, large numbers of photons are usually required to achieve acceptable noise to signal ratios in the reconstructed images ($\sigma_F/F \sim 0.01\%$ to 10%), it is preferred that G of the detector to be greater than 0.05 to achieve practical exposure times. In a more preferred embodiment, G is greater than 0.5 and exposure times are within a factor of four of those achieved with an ideal detector (G=1). Methods to measure the detective quantum efficiency of an electro-optic x-ray detector have been described by S. M. Gruner and J. R. Milch, Transactions of the American Crystallographic Association, Vol. 18, 1982.

A signal dependent background exists in all electro-optic x-ray detectors due to scattering of radiation between the energy conversion process and detection at the electro-optic readout device. Scattered radiation which produces a signal dependent background may have a component which is spatially correlated with the signal as well as a component which is spatially uncorrelated with the original signal. Because optimal observation conditions occur when the optical density through the target is nearly equal to 2 (13.5% transmission), the total signal dependent background (correlated+uncorrelated) in any pixel covered by the sample must be less than 10% of that from the unattenuated x-ray beam. In a more preferred embodiment, the total signal dependent background (correlated+uncorrelated) in any pixel covered by the sample is less than 2% of the signal derived from the unattenuated x-ray beam. Signal dependent backgrounds for an electro optic x-ray detector can be measured using a variety of techniques. A simple technique is to cover half the incident x-ray beam with a mask which totally absorbs x-rays. In principle, there should be no signal in the region covered by the mask, and signal levels detected in the region behind the mask are clearly due to the correlated and uncorrelated backgrounds. Far from the mask edge the signal dependent background slowly varies and is primarily due to the uncorrelated signal level. Near the mask edge spatial variation of the signal dependent background is a direct measure of the correlated scattered light. Thus, by fitting a spatial correlation function to the signal dependent background near the mask edge, the correlated and uncorrelated signal dependent backgrounds can be quantified.

Useful dynamic range of the detector is defined as the ratio of maximum signal level recorded in an exposure to the sum of all signal dependent backgrounds and noise source (other than counting statistics). By minimizing noise from sources other than counting statistics, the useful dynamic range is maximized. Examples of noise sources other than counting statistics are readout and dark noise. Dark noise accumulates with time in the absence of an input signal and can severely limit maximum exposure time. Readout noise is an uncertainty added to the signal during readout of the sensor used to record optical images. The readout device with the lowest dark and readout noise is a charge coupled device (CCD). Readout and dark noise of CCD sensors is at least an order of magnitude lower than vacuum tube TV sensors such as vidicons. As such CCD sensors are most preferred for construction of imaging electro-optic x-ray detectors. Since under optimal observation conditions, signals which are 13% of the unattenuated beam must be recorded, the useful dynamic range of the detector must be greater than 10. In a more preferred embodiment, the useful dynamic range of the detector is greater than 50.

Most detectors are not uniformly sensitive across their area. If the non-uniformity of response between adjacent pixels is not calibrated out of the data, then artifacts will be generated in the reconstruction process. A stable 10% non-uniformity between adjacent active pixels is easily calibrated out of the data. However, when the non-uniformity of response between adjacent active pixels exceeds 75%, calibration methods fail to work. The failure of calibration methods for deeply modulated non-uniformities between adjacent pixels is due to stability considerations of the detector. Vibrations, spatial drifts, and time dependent drifts of the sensitivity, all decrease the stability of the detector so that deeply modulated non-uniformities between adjacent pixels cannot be readily removed from the data. As such, it is preferred that the non-uniformity of response between adjacent active pixels be less than 75%. Limits also exist on variations of the locally averaged sensitivity across the detector surface. The locally averaged sensitivity is defined as the average of the sensitivity of an active pixel and its immediately adjacent neighbors. From signal to noise considerations it is preferred that the locally averaged sensitivity varies by no more than a factor of 2 across the entire detector surface. Variations in the locally averaged sensitivity across the detector surface lead to a variation in the signal to noise ratio in the detected signal. To optimize performance of the device it is desired that the fewest possible x-ray photons be required for reconstruction of a target at a given signal to noise ratio. When the locally averaged sensitivity varies across the detector, the required number of x-ray photons corresponds most closely with that expected for the minimum average sensitivity. Regions of minimum locally averaged sensitivity generally correspond to defects in the detector. Thus, to minimize exposure time and optimize performance of the tomography system, it is desired that the variations in the locally averaged sensitivity across the detector be less than 10 and in a more preferred embodiment be less than 2.

When geometric distortions from true positional linearity of the pixels within the detector become too large the reconstruction algorithms fail to produce an adequate representation of the original target. Artifacts are introduced from uncorrected positional non-linearities because the impact parameters, $t_1$, (see FIG. 3) are systemmatically mismeasured. This mismeasurement occurs whenever a Cartesian grid imaged through the electro-optic detector deviates from linearity by more than one pixel position. For small deviations from true positional linearity a distortion map can be applied to the data to correct the impact parameters so that the data is acquired on a true Cartesian grid. This correction becomes impractical when the deviation from linearity exceeds 10 pixel positions across the detector surface. As such, it is preferred that deviations from true geometric linearity be less than 10 pixels in the recorded image. In a more preferred embodiment, impact parameters are accurately measured at the detector surface and the maximum deviation from geometric linearity is less than 1 pixel in the recorded image.

The aforementioned detector attributes of: (1) quantum detection efficiency, (2) signal dependent backgrounds in the recorded image, (3) useful dynamic range of the detector, (4) spatial uniformity of response, and (5) positional linearity, severely limit the number of electro-optic detector configurations which can be used in tomography systems. Other important detector attributes are: (1) linearity of response vs. intensity, (2) stability of the response vs. intensity, (3) spatial resolution and (4) count rate limitations. Preferred ranges of these detector attributes will be discussed in the following paragraphs.

The detector response vs. X-ray intensity must be linearized to accurately measure the projections which are defined in Equation 2. The projection measurements form the basis for the tomographic inversion methods. Projection measurements can only be accurately obtained when the detector response is linearized. Detector response vs. incident X-ray dose can be linearized by appropriate calibration methods when the deviations from linearity are less than 25% over the useful dynamic range of the detector. When deviations from linearity exceed 200% anywhere within the useful dynamic range of the detector, calibration techniques fail to adequately correct the data. Failure to adequately linearize the detector response when deviations from linearity exceed a factor of 2 generally stem from change of the response with time. In all electro-optic detectors, response changes slightly with time. This is due to radiation damage in the energy convertor plate and time dependent changes in the amplification of the gain element and read out device. The time dependent changes in the detector response must be such that between two successive calibration frames the percentage change in the detective quantum efficiency is less than the desired noise to signal ratio. Calibration frames are acquired to measure the intensity of the incident X-ray beam, $I_O$ and may be taken as often as once per angular rotation of the target or as infrequently as once per 180 degree rotation of the target. To obtain a calibration frame, the sample is withdrawn from the X-ray beam and the unattenuated X-ray intensity is measured.

Spatial resolution of the detector is determined primarily by the format alteration technique used to couple the energy convertor plate and readout device. Adjustability of the detector resolution through simple format alteration is a key advantage of electro-optic X-ray detectors over the more conventional scintillation detectors which have been used in tomography. Format alterations can be performed using either electron or light optics. Simplest of all optical format alteration techniques is a lens system which couples light from a phosphor screen directly onto a readout device with no intervening image intensifier. This system is well-suited for magnification of images formed on high resolution phosphor screens and can achieve spatial resolutions comparable to the wavelength of light (approximately 0.5 microns). This limiting spatial resolution can only be achieved with extremely high resolution phosphor screen which are ideally formed as a honeycombed array of phosphor plugs having dimensions comparable to or smaller than the desired spatial resolution. By fabricating the phosphor screen as a honeycombed array of individual phosphor cells (a cellular phosphor) degradation of resolution by light scattering within the phosphor can be eliminated. In this case, the limiting resolution is then determined by the numerical aperture of the relaying lens system which can be 0.6–0.8 yielding ultimate spatial resolutions of approximately 0.5 microns. Lower resolutions can be achieved by decreasing the magnification of the lens system and coarsest resolutions are achieved by using demagnifying rather than magnifying lens systems. A restriction exists on the maximum demagnification attainable in a simple lens coupled electro-optic detector. Restriction of the useful demagnification range is due to an inherent limitation of the light gathering efficiency from lenses. The optical brightness theorem dictates that the maximum light gathering efficiency, $L_e^{max}$ for an ideal lens viewing a lambertin intensity distribution from a phosphor is $L_e^{max} = M^2$ (if $M << 1$) where M is the magnification factor which is the reciprocal of the demagnification factor. Light gathering efficiencies, $L_e$, of actual lenses are significantly less than this limit. Light transfer efficiencies of most lenses can be approximated by either $L_e = (NA)^2$ or $L_e = (M/2f)^2$ where NA is the numerical aperture of the lens and f is the f number of the lens. For large demagnification factors this limitation dictates that a lens will relay only a small fraction of the number of optical photons generated in the phosphor plate. With only a small fraction of the number of generated photons reaching the readout device, the detective quantum efficiency will be significantly reduced. The reduction can be so great as to fall outside the preferred range of $D > 0.05$. In theory, limitations found for demagnification in lens coupled format alterations could be overcome with fiber optic coupling. Light gathering efficiency of lenses are far below theoretical limits imposed by the optical brightness theorem: whereas fiber optic reducing bundles closely approach this limit due to their high numerical aperture. Light transfer efficiency of a reducing fiber optic bundle is approximately given by either $L_e = (NA_{input})^2$ or $L_e = (M \times NA_{output})^2$ where $NA_{input}$ ($NA_{output}$) is the input (output) numerical aperture. Improved light gathering efficiency of fiber optic bundles results in a higher detective quantum efficiency than can be achieved with similar format alterations in lens coupled systems. However, usefulness of fiber optic coupling is limited by distortions in the fiber packing which occur during the fabrication of reducing bundles. Usually reducing bundles are drawn from fiber optic blanks which are created by sintering bundles of individual fibers. In this process both localized and extended defect structures are formed. Localized defect structures include broken fibers, distortions of fiber packing within bundles and dislocation defects in bundle packing. Extended defect structures generated in the drawing process produce pin cushion and barrel distortion of images relayed through the reducing bundle. In many cases these geometric distortions produce positional non-linearities greater than 10 pixels and as such are unacceptable for tomographic systems. In order to overcome format reduction limitations for lens systems and not suffer distortions introduced by fiber optics, it is advantageous to incorporate an intensifier stage between the energy convertor plate (phosphor) and readout device. Available intensifiers include micro channel plates, and magnetically and electrostatically focused intensifiers. All of these intensifiers can be used in a mode where the X-ray image is relayed with no format alteration to a lens which reduces the image. In this mode, the gain of the intensifier overcomes the limitations on the detective quantum efficiency imposed by the light gathering efficiency of the lens system used to reduce the image. Image reduction can also be conveniently accomplished within the intensifier when electrostatic focusing is utilized. This technology has advanced significantly due to the development of SIT tubes and at present format reductions of 2:1 are widely available. Custom built electrostatically focused intensifiers can have reduction factors greater than 2:1, however, aberations in the electrostatic focusing lens limit the maximum reduction ratio.

Electro optical detectors offer a flexible modluar approach to quantitative X-ray detection. The previous discussion has defined for one skilled in the art, detector configurations which can be used in a tomography apparatus. In designing electro optic X-ray detectors for tomography, it is preferable to use a charge couple device (CCD) as the readout device. In recent years, solid state charge coupled devices have evolved to become the pre-eminent imaging electro optical sensor technology. CCD sensors are attractive for X-ray detection application in that they offer significant improvements over other TV sensors such as vidicons, isocons and orthocons. The readout and dark noise is at least an order of magnitude lower than the vacuum tube TV sensors thereby improving the sensor detective quantum efficiency. Commercially available CCD sensors have a readout noise of less than 50 electrons/pixel and a dark noise of less than 5 electrons/minute-pixel when operated at temperatures below $-75°$ C. CCD sensors also exhibit the largest dynamic range (saturation signal/r.m.s. readout noise) of all electro optic sensors. Saturation signals on many CCD sensors approach $10^6$ electrons/pixel yielding a dynamic range for signal detection of approximately $10^5$. On some chips a limitation exists when the saturation level is approached, due to the lack of an ability to locally saturate pixels. For signal levels below saturation, CCD sensors exhibit an exceptional linearity of response with respect to light input intensity. Finally, because the light sensing elements are fixed on the CCD chip, one avoids geometric distortions associated with electron beam readout of vacuum TV tubes.

EXAMPLES

Example 1

Figure 7:
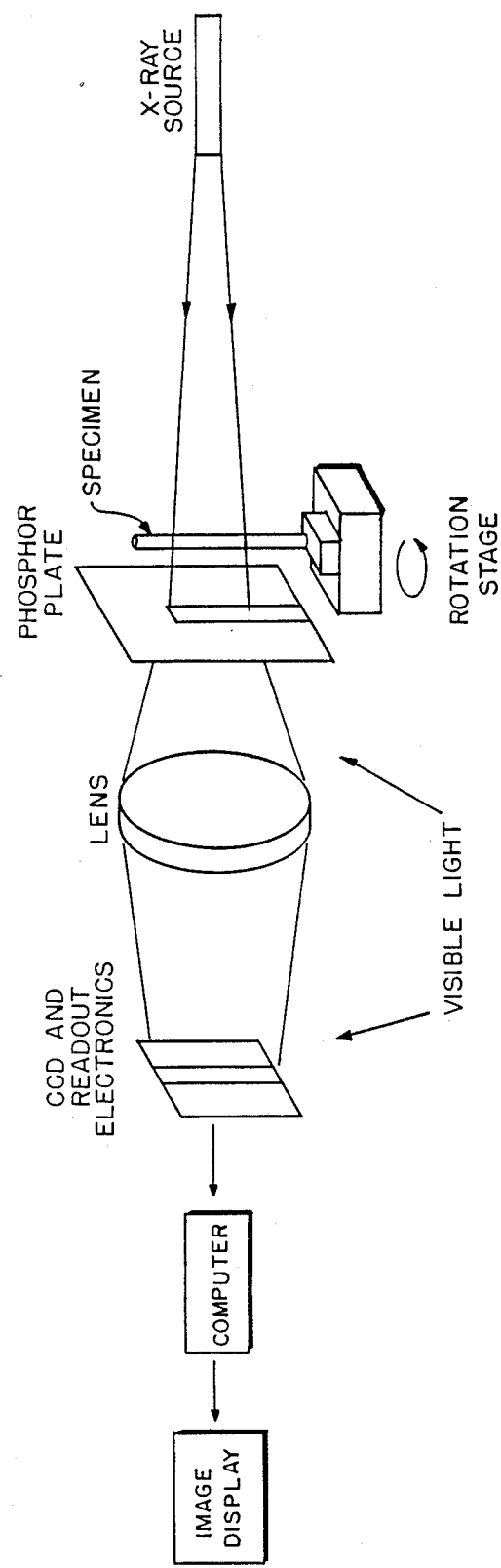
FIG. 7—Schematic diagram of an X-ray microtomography apparatus constructed with an electro-optic detector.

A schematic diagram of an X-ray micro tomography system constructed with an electro optic X-ray detector is shown in FIG. 7. X-rays are generated from a Cu fine focus X-ray tube manufactured by Phillips Electronic Instruments. The tube was aligned to present a point X-ray source to the experiment and was operated at a power of 1.5 kw. The distance between the X-ray source and specimen was chosen to be 20 cm and the tube was positioned so that the line connecting the center of the point X-ray source and center of the portion of the specimen being imaged was perpendicular to the axis of rotation of the specimen. Take-off angle of the experiment with respect to the anode shadow projected by the tube was approximately 5° yielding an effective X-ray source size of approximately 750 microns by 500 microns. The sample was held on a rotatable goniometer within the X-ray beam. The rotation stage was controlled with stepping motors which can move the stage in increments as small as 0.01°. For a full 360° rotation of the rotary stage, wobble in the axis of rotation was less than $10^{-5}$ radians. For such an infinitesimal wobble, the axis of rotation remains fixed in space and does not translate as the sample is rotated. On the goniometer the sample was aligned so that it remained within the lateral field of view as the sample was rotated. The sample mounted on the goniometer was a 750 micron diameter hollow glass tube which was packed with approximately 200 micron diameter silica spheres along with a 10 micron tungsten wire which ran along the axis of the tube. A phosphor conversion plate was located 2 mm behind the sample. The phosphor was a 5 micron thick layer of evaporated CsI doped with thalium. Light emanating from the phosphor conversion plate was imaged by a photographic lens onto a charged coupled device. To maximize detective quantum efficiency a photographic lens with a f number of 1.4 was chosen. Magnification of the lens system was adjusted so that an 8 micron element on the phosphor plate was magnified to 30 microns which is the pixel size of the CCD. The CCD used in these experiments was a RCA SID-501 which has 336 by 540 active pixel elements. It was aligned so that the columns of the device were parallel to the axis of rotation of the specimen. With this geometric arrangement of the apparatus, the angular deviation $\alpha$ of 2 principle rays through different points in the sample was $2.5 \times 10^{-2}$ radians, which as required by Equation 13 is less than 2 $\Delta t/D = 4.26 \times 10^{-2}$ radians. Angular divergence, $\alpha'$, of 2 rays through the same point in the sample is $3.75 \times 10^{-3}$ radians which as required by Equation 14 is less than $\Delta t/S = 4 \times 10^{-3}$ radians. Thus, data is acquired in multiple stacked planes in the plane parallel mode. The number of equally spaced view angles, M, required for data acquired in this mode, must be greater than $\pi N/2$, wherein N is the number of equally spaced discrete parallel impact parameters spanning the target. Since the target is 750 microns in diameter and each pixel spans 8 microns, approximately 85 impact parameters span the target. To satisfy the protocol for data acquisicioned in the plane parallel mode, 240 equally spaced view angles ($\Delta\phi$) were chosen to scan the target.

Detective quantum efficiency of the detector was measured to be 0.75 and the total signal dependent background was found to be less than 2 percent of the signal from the unattenuated x-ray beam. Useful dynamic range of this detector configuration was a factor of 80 and the maximum non-uniformity of response between adjacent active pixels was less than 5 percent. No detectable image distortions were introduced in lens coupling the phosphor plate to the CCD so that the maximum deviation of geometric linearity was less than 1 pixel in the recorded image. Data, with a noise to signal ratio of 0.3% was obtained in the detector by exposing each view angle for 3 minutes. Data from each view angle was digitized with a 16 bit analog to digital convertor, processed by a computer and stored on a magnetic tape. Image reconstruction was then performed utilizing Direct Fourier Inversion methods (DFI) which have an operations count of $N^2$, rather than $N^3$.

FIG. 8 shows projection data acquired in one view of the hollow glass tube as well as cross sectional views at the points indicated in the Figure. It is seen that the 200 micron glass spheres are clearly visible in the cross-sectional images as well as the 10 micron tungsten wire. Spatial resolution achieved in this reconstruction is more than 25 times better than that achieved with conventional medical CAT scanners.

What is claimed is:

1. An apparatus for producing three dimensional tomographic images of an object irradiated by a plurality of rays of plane parallel collimated radiation (unattenuated beam) transmitted through said object comprising:
   (a) a two-dimensional electro-optical imaging detector having active pixels for simultaneously recording a two-dimensional image that measures attenuated transmitted radiation from multiple stacked planes after said plane parallel collimated radiation has passed through the object, said detector including an energy converter, an image format altering device, and a readout device, wherein said detector's active pixels have a detective quantum efficiency greater than 0.05, a total signal dependent background less than 10 percent of the signal from the unattenuated beam and a useful dynamic range greater than 10, and deviations of geometric linearity that are less than 10 pixels in the recorded image;
   (b) means for obtaining projection data from said attenuated transmitted radiation, and
   (c) means for computing a three dimensional reconstructed image of attenuation coefficients of said object from said projection data.

2. The apparatus of claim 1 wherein said detector's active pixels have a non-uniformity of response between adjacent active pixels of less than 75%.

3. The apparatus of claim 1 further including a source of radiation.

4. The apparatus of claim 3 wherein said source of radiation is an x-ray source.

5. The apparatus of claim 3 wherein said source of radiation is rigidly connected to said electro-optical detector.

6. The apparatus of claim 5 further comprising a means to rotate one of said object or said source of radiation about an axis.

7. The apparatus of claim 1 wherein said detector further comprises a gain element.

8. The apparatus of claim 1 wherein said detector has a detective quantum efficiency greater than 0.5.

9. The apparatus of claim 1 wherein said detector has a signal dependent background less than 2%.

10. The apparatus of claim 1 wherein said detector has a dynamic range greater than 50.

11. The apparatus of claim 1 wherein said detector has a deviation of geometric linearity less than 1 pixel.

12. The apparatus of claim 1 wherein said readout device is a charge coupled device.

13. The apparatus of claim 1 wherein the active pixels have a maximum non-uniformity of response across the detector of less than 10%.

14. The apparatus of claim 1 wherein the active pixels have a maximum non-uniformity of response across the detector of less than 2%.

15. The apparatus of claim 1 wherein said electro-optical detector includes a cellular phosphor.

16. The apparatus of claim 1 further including a display device.

* * * * *